(12) United States Patent
Davis et al.

(10) Patent No.: US 11,491,436 B2
(45) Date of Patent: Nov. 8, 2022

(54) PORTABLE MICRO-PRECONCENTRATOR TO FACILITATE CHEMICAL SAMPLING AND SUBSEQUENT ANALYSIS

(71) Applicant: The Regents of the University of California, Oakland, CA (US)

(72) Inventors: Cristina E. Davis, Davis, CA (US); Michael K. Levasseur, Davis, CA (US); Raquel Cumeras, Tarragona (ES); Yuriy Zrodnikov, West Sacramento (CA); Mitchell M. McCartney, Davis, CA (US); Alexander G. Fung, Davis, CA (US); Daniel J. Peirano, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/157,595

(22) Filed: Jan. 25, 2021

(65) Prior Publication Data
US 2021/0316246 A1 Oct. 14, 2021

Related U.S. Application Data

(62) Division of application No. 16/087,054, filed as application No. PCT/US2017/023908 on Mar. 23, 2017, now Pat. No. 10,940,428.
(Continued)

(51) Int. Cl.
*B01D 53/04* (2006.01)
*B01L 3/00* (2006.01)
(Continued)

(52) U.S. Cl.
CPC ......... *B01D 53/0438* (2013.01); *A61B 5/082* (2013.01); *B01D 53/0454* (2013.01); *B01L 3/502707* (2013.01); *B01L 7/00* (2013.01); *G01N 1/405* (2013.01); *G01N 27/624* (2013.01); *G01N 33/497* (2013.01); *B01D 2259/4525* (2013.01); *B01D 2259/4566* (2013.01);
(Continued)

(58) Field of Classification Search
CPC ............ B01D 53/0438; B01D 53/0454; B01D 2259/4525; B01D 2259/4566; A61B 5/082; B01L 3/502707; B01L 7/00; B01L 2200/12; G01N 1/405; G01N 27/624; G01B 33/497
See application file for complete search history.

(56) References Cited

U.S. PATENT DOCUMENTS 4,752,761 A * 6/1988 Dolan .................... G01N 27/12
29/592.1
5,142,143 A * 8/1992 Fite ........................ G01M 3/202
250/281

(Continued)

*Primary Examiner* — Jonathan Miller
(74) *Attorney, Agent, or Firm* — Park, Vaughan, Fleming & Dowler LLP

(57) ABSTRACT

The disclosed embodiments relate to the design of a preconcentrator system for preconcentrating air samples. This preconcentrator system includes a plurality of preconcentrators that preconcentrate the air samples prior to chemical analysis, and a delivery structure comprising a manifold that selectively routes a sample airflow to the plurality of concentrators so that the plurality of preconcentrators receive a sample airflow concurrently or individually.

15 Claims, 10 Drawing Sheets

Related U.S. Application Data

(60) Provisional application No. 62/313,523, filed on Mar. 25, 2016, provisional application No. 62/313,481, filed on Mar. 25, 2016, provisional application No. 62/313,527, filed on Mar. 25, 2016, provisional application No. 62/313,513, filed on Mar. 25, 2016, provisional application No. 62/313,432, filed on Mar. 25, 2016, provisional application No. 62/313,442, filed on Mar. 25, 2016, provisional application No. 62/313,457, filed on Mar. 25, 2016, provisional application No. 62/313,486, filed on Mar. 25, 2016, provisional application No. 62/313,489, filed on Mar. 25, 2016, provisional application No. 62/313,495, filed on Mar. 25, 2016, provisional application No. 62/313,507, filed on Mar. 25, 2016, provisional application No. 62/313,517, filed on Mar. 25, 2016.

(51) Int. Cl.
*B01L 7/00* (2006.01)
*G01N 1/40* (2006.01)
*G01N 27/624* (2021.01)
*G01N 33/497* (2006.01)
*A61B 5/08* (2006.01)

(52) U.S. Cl.
CPC ....... *B01L 2200/12* (2013.01); *B01L 2300/06* (2013.01); *B01L 2300/0627* (2013.01); *B01L 2300/12* (2013.01); *B01L 2300/1805* (2013.01); *B01L 2300/1894* (2013.01)

(56) References Cited

U.S. PATENT DOCUMENTS

| | | | |
|---|---|---|---|
| 6,074,725 A * | 6/2000 | Kennedy | B01L 3/502707 156/277 |
| 6,527,835 B1 * | 3/2003 | Manginell | G01F 1/6845 55/524 |
| 7,147,695 B2 * | 12/2006 | Mitra | G01N 30/12 96/101 |
| 9,244,051 B2 * | 1/2016 | Josse | G01N 33/1826 |
| 10,694,978 B2 * | 6/2020 | Ahmad | A61B 5/097 |
| 2004/0194628 A1 * | 10/2004 | Mitra | G01N 30/12 96/101 |
| 2005/0045030 A1 * | 3/2005 | Tonkovich | B82Y 30/00 95/90 |
| 2007/0048181 A1 * | 3/2007 | Chang | G01N 27/4146 422/400 |
| 2008/0007728 A1 * | 1/2008 | Schneider | G01N 1/2273 356/301 |
| 2011/0214482 A1 * | 9/2011 | Martin | G01N 1/405 73/25.05 |
| 2012/0216597 A1 * | 8/2012 | Park | G01N 1/405 73/23.41 |
| 2014/0011285 A1 * | 1/2014 | Josse | G01N 1/405 436/139 |
| 2016/0331272 A1 * | 11/2016 | Ahmad | A61B 5/097 |
| 2017/0229375 A1 * | 8/2017 | Haj-Hariri | H01L 23/427 |
| 2017/0303822 A1 * | 10/2017 | Allsworth | B01D 46/0028 |

\* cited by examiner

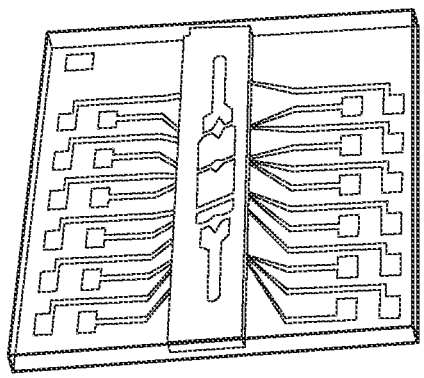
FIG. 5A
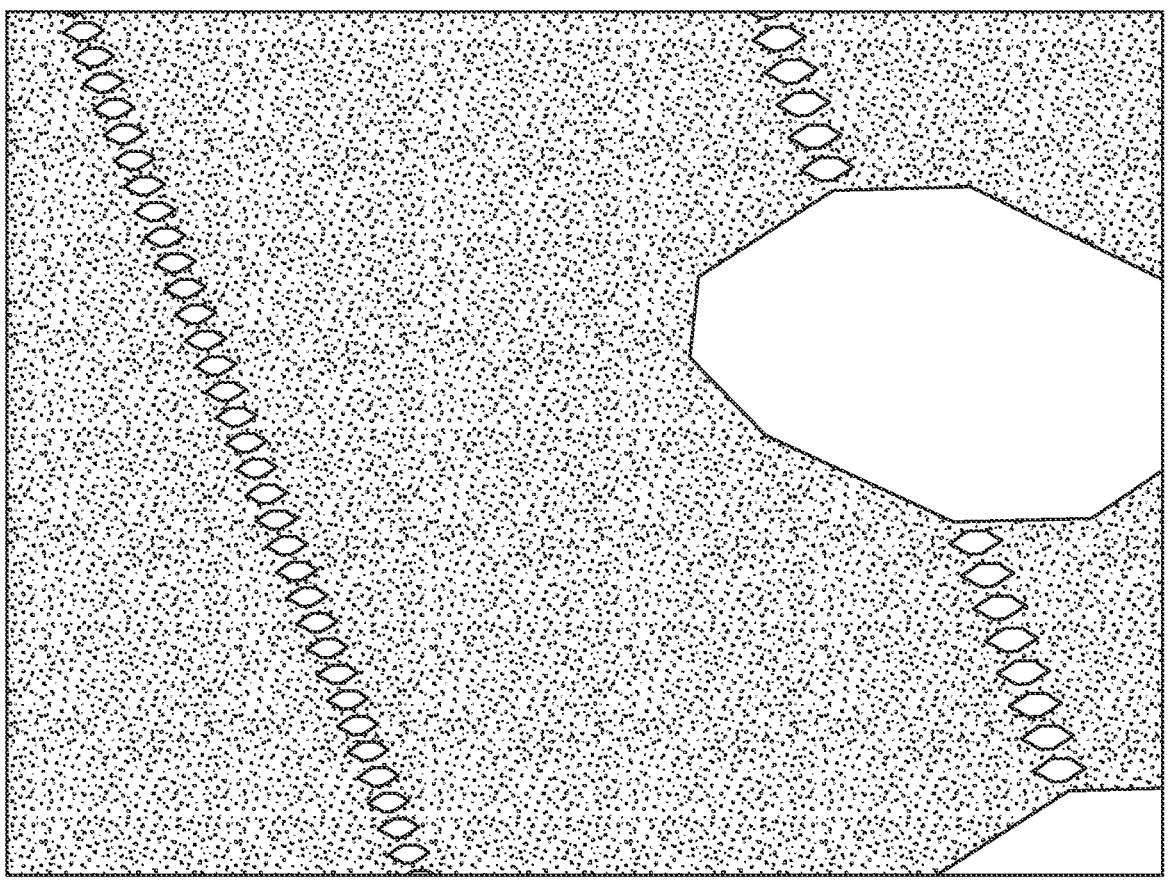
FIG. 5B

PORTABLE MICRO-PRECONCENTRATOR TO FACILITATE CHEMICAL SAMPLING AND SUBSEQUENT ANALYSIS

RELATED APPLICATIONS

This application is a divisional application of, and hereby claims priority under 35 U.S.C. § 120 to, pending U.S. patent application Ser. No. 16/087,054, which has the same title and inventors as the instant application, filed on 20 Sep. 2018, which is hereby incorporated by reference. U.S. patent application Ser. No. 16/087,054 itself claims priority to PCT application No. PCT/US17/23908 filed on Mar. 23, 2017. PCT Application No. PCT/US17/23908 itself claims priority under 35 U.S.C. § 119 to the following U.S. provisional patent applications: Application No. 62/313,523, filed 25 Mar. 2016; Application No. 62/313,481, filed 25 Mar. 2016; Application No. 62/313,527, filed 25 Mar. 2016; Application No. 62/313,513, filed 25 Mar. 2016; Application No. 62/313,507, filed 25 Mar. 2016; Application No. 62/313,517, filed 25 Mar. 2016; Application No. 62/313,432, filed 25 Mar. 2016; Application No. 62/313,442, filed 25 Mar. 2016; Application No. 62/313,457, filed 25 Mar. 2016; Application No. 62/313,486, filed 25 Mar. 2016; Application No. 62/313,489, filed 25 Mar. 2016; and Application No. 62/313,495, filed 25 Mar. 2016. The contents of the above-listed applications are incorporated by reference herein in their entirety.

BACKGROUND

Field

The disclosed embodiments generally relate to systems for gathering and analyzing chemical samples. More specifically, the disclosed embodiments relate to the design of a micro-preconcentrator, which facilitates gathering and storing chemical samples to facilitate subsequent chemical-analysis operations.

Related Art

Chemical-analysis techniques, such as ion-mobility spectrometry (IMS) and gas chromatography (GC), presently make it possible to produce analytic systems that are able to identify complex chemical compounds with a high degree of accuracy. However, it is often difficult to test samples for vapor-phase chemical compounds because of their diffuse concentrations. This difficulty can be addressed by installing a "preconcentrator" at the front end of an analytical system to significantly enhance the detection performance by trapping and concentrating analytes.

Recent technological developments are presently making it possible to produce significantly smaller IMS and GC systems. This is making it possible to deploy chemical-detection systems in the field instead of in a laboratory, which provides significant advantages in diverse applications, such as detecting the presence of chemical weapons or human-breath analysis. However, corresponding portable preconcentrator designs need to be developed to make such portable chemical-analysis systems practical.

SUMMARY

The disclosed embodiments relate to the design of a preconcentrator system for preconcentrating air samples. This preconcentrator system includes a plurality of preconcentrators that preconcentrate the air samples prior to chemical analysis, and a delivery structure that delivers the air samples to the plurality of preconcentrators.

In some embodiments, the delivery structure allows the plurality of preconcentrators to receive a sample airflow concurrently or individually.

In some embodiments, the delivery structure comprises a manifold that selectively routes a sample airflow to the plurality of concentrators.

In some embodiments, the delivery structure comprises a rotating component that holds the plurality of preconcentrators, wherein the rotating component is rotatable to move each preconcentrator into a position to receive a sample airflow.

In some embodiments, the delivery structure connects the plurality of preconcentrators so that a sample airflow passes through the plurality of preconcentrators in parallel.

In some embodiments, the delivery structure connects the plurality of preconcentrators so that a sample airflow passes through the plurality of preconcentrators in series.

In some embodiments, the delivery structure controls a sampling time for each of the plurality of preconcentrators.

In some embodiments, the preconcentrator system is integrated into an unmanned aerial system.

In some embodiments, a flight path of the unmanned aerial system is controllable to facilitate gathering samples of interest.

In some embodiments, the preconcentrator system includes at least one pump to facilitate propagating a sample airflow through the plurality of preconcentrators.

In some embodiments, different sorbent materials are used in the plurality of preconcentrators for different applications.

In some embodiments, the preconcentrator system further comprises one or more heaters to trigger a release of absorbed compounds from the sorbent material contained in the one or more preconcentrators.

In some embodiments, the preconcentrator system performs labeling operations to label the gathered air samples.

In some embodiments, the preconcentrator system incorporates Global Positioning System (GPS) data into the gathered air samples.

The disclosed embodiments also relate to another design for a preconcentrator, comprising an etched substrate, wherein the etched substrate includes: one or more channels for sample airflow; one or more cavities for holding a sorbent material; one or more inlet holes for sample airflow; one or more outlet holes for sample airflow; and one or more heaters integrated into the etched substrate.

In some embodiments, the preconcentrator is constructed using microfabrication techniques.

In some embodiments, the one or more heaters comprise resistive heaters.

The disclosed embodiments also relate to another design for a preconcentrator system, comprising a substrate that is micro-machined to include consecutive cavities containing sorbent material, wherein the consecutive cavities are separated by micro-pillars. During a sampling operation, a gas phase sample passes through the consecutive cavities containing the sorbent material. The preconcentrator system also includes a mouthpiece and a tube, which are coupled to the preconcentrator for receiving human-breath samples.

In some embodiments, each of the consecutive cavities includes an inlet and an outlet, wherein micro-pillars at the inlet and the outlet function to support and contain sorbent material in the cavity.

In some embodiments, each of the consecutive cavities holds a different type of sorbent material.

In some embodiments, one or more of the consecutive cavities is used with a molecular sieve to retain water content from a sample.

In some embodiments, the preconcentrator system further comprises a humidity sensor and/or a temperature sensor located at an inlet of the preconcentrator to trigger a breath sample.

In some embodiments, the preconcentrator system further comprises an integrated heater that triggers a release of absorbed compounds from the sorbent material.

In some embodiments, the integrated heater is controlled using a feedback-based temperature-control technique.

In some embodiments, the integrated heater includes electrodes that face the sorbent material in the cavities to decrease power consumption.

In some embodiments, the integrated heater includes electrodes having a fractal structure.

In some embodiments, the preconcentrator system further comprises a pump to facilitate moving a sample through the preconcentrator system.

The disclosed embodiments also relate to another design for a preconcentrator system for preconcentrating gas samples for agricultural applications. This preconcentrator system comprises a substrate, which includes: one or more channels for accommodating a sample flow, wherein the one or more channels are coated with a sorbent material so that the sorbent material can be exposed to the sample flow; and one or more heaters for heating the sorbent material.

In some embodiments, the sample flow includes one or more of: gas samples outgassed from plants in a greenhouse; gas samples outgassed from plants in an orchard; gas samples obtained during post-harvest transportation of agricultural products; and gas samples obtained during post-harvest storage of agricultural products.

In some embodiments, a sorbent type and a sampling temperature are controllable during sampling to promote capture of volatile organic compounds of interest over extraneous chemicals.

In some embodiments, the preconcentrator system further comprises an external cooling supply.

In some embodiments, the one or more heaters trigger a release of absorbed compounds from the sorbent material.

In some embodiments, the one or more heaters are fabricated by depositing a conductive material on the substrate.

In some embodiments, the one or more heaters uniformly heat an active area.

In some embodiments, the preconcentrator system further comprises one or more temperature sensors, and a feedback-based temperature control system that uses readings from the one or more temperature sensors to control the one or more heaters.

In some embodiments, the one or more channels comprise high-aspect-ratio, porous microstructures for holding the sorbent material.

In some embodiments, the high-aspect-ratio microstructures include channels that are about 300 micrometers tall and 10 micrometers wide.

In some embodiments, the preconcentrator system comprises multiple preconcentrators.

In some embodiments, the multiple preconcentrators are programmable to separately sample during different time slots.

In some embodiments, the one or more heaters are programmable to either: apply heat rapidly to instantly desorb chemicals from the sorbent material; or apply heat gradually to control a release of different compounds at different times from the sorbent material.

The disclosed embodiments also relate to a system and method for controlling environmental parameters in a shipping container. During the method, the system: gathers samples of compounds off-gassed from products stored in the shipping container; uses a chemical detector to measure concentrations of volatile compounds-of-interest in the samples; and performs closed-loop control of at least one environmental parameter in the shipping container based on the measured concentrations.

In some embodiments, the at least one environmental parameter includes one or more of the following: temperature, humidity, air ventilation rates, atmospheric gas composition, and light.

In some embodiments, using the chemical detector to measure the concentrations of volatile compounds-of-interest includes using one or more of the following: a gas chromatograph; an ion mobility spectrometer; a differential mobility spectrometer; a high asymmetric longitudinal field ion mobility spectrometer (HALF-IMS); a high field asymmetric ion mobility spectrometer (FAIMS); an electronic nose (E-nose); and an ethylene detector.

In some embodiments, controlling the at least one environmental variable includes controlling one or more of the following for the shipping container: a refrigeration unit; a heater; a humidifier; a light source; and a ventilation system.

In some embodiments, the closed-loop control is performed to mitigate spoilage of the products stored in the shipping container.

In some embodiments, the closed-loop control is performed to reduce energy usage in the shipping container.

In some embodiments, the closed-loop control is performed to reduce the effects of malodors on the products stored in the shipping container.

In some embodiments, the closed-loop control is performed to optimize a ripening process for the products stored in the shipping container.

In some embodiments, the method further comprises using the measured concentrations of the volatile compounds-of-interest to detect disease contamination in the products stored in the shipping container.

In some embodiments, the method further comprises producing a log of volatile compound concentrations monitored during a shipment involving the shipping container.

In some embodiments, the method further comprises: determining from the measured concentrations of the volatile compounds-of-interest whether the products stored in the shipping container have spoiled; and if the products have spoiled, discontinuing the power used to control the at least one environmental parameter.

BRIEF DESCRIPTION OF THE FIGURES

FIG. 5A presents a photograph of an exemplary preconcentrator in accordance with the disclosed embodiments.

FIG. 5B presents a photograph illustrating etched micropillars in an exemplary preconcentrator in accordance with the disclosed embodiments.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

Chemical-Analysis System

Figure 1:
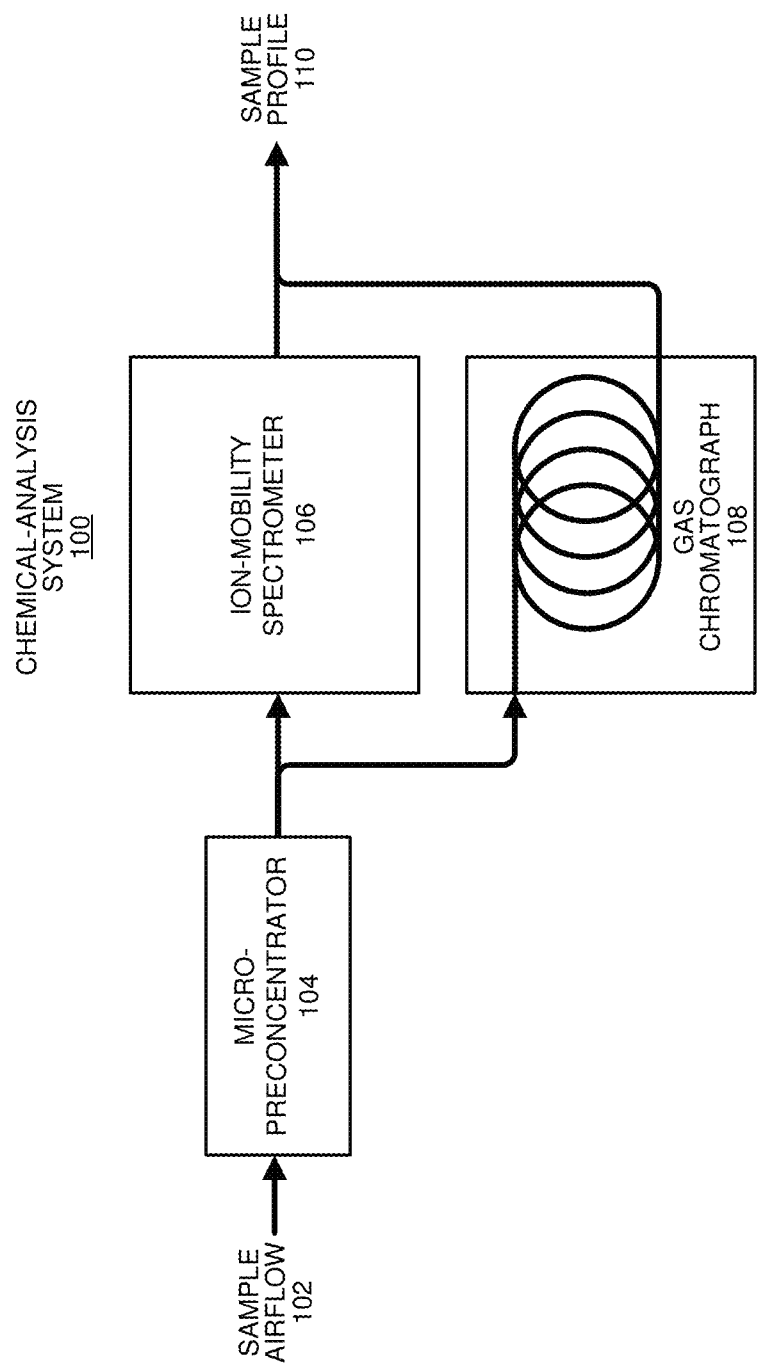
FIG. 1 illustrates a chemical-analysis system in accordance with the disclosed embodiments.

FIG. 1 illustrates an exemplary chemical-analysis system 100 in accordance with the disclosed embodiments. During operation, chemical-analysis system 100 receives a sample airflow 102, which is directed through a micro-preconcentrator 104, which traps and concentrates analytes from the sample airflow 102. Next, the output of micro-preconcentrator 104 feeds into an ion-mobility spectrometer 106, which produces a set of measured values for analytes in the preconcentrated sample to form a sample profile 110. As illustrated in FIG. 1, the output of micro-preconcentrator 104 can also feed into a gas chromatograph 108, which similarly measures values for analytes to add to the sample profile 110.

Figure 2:
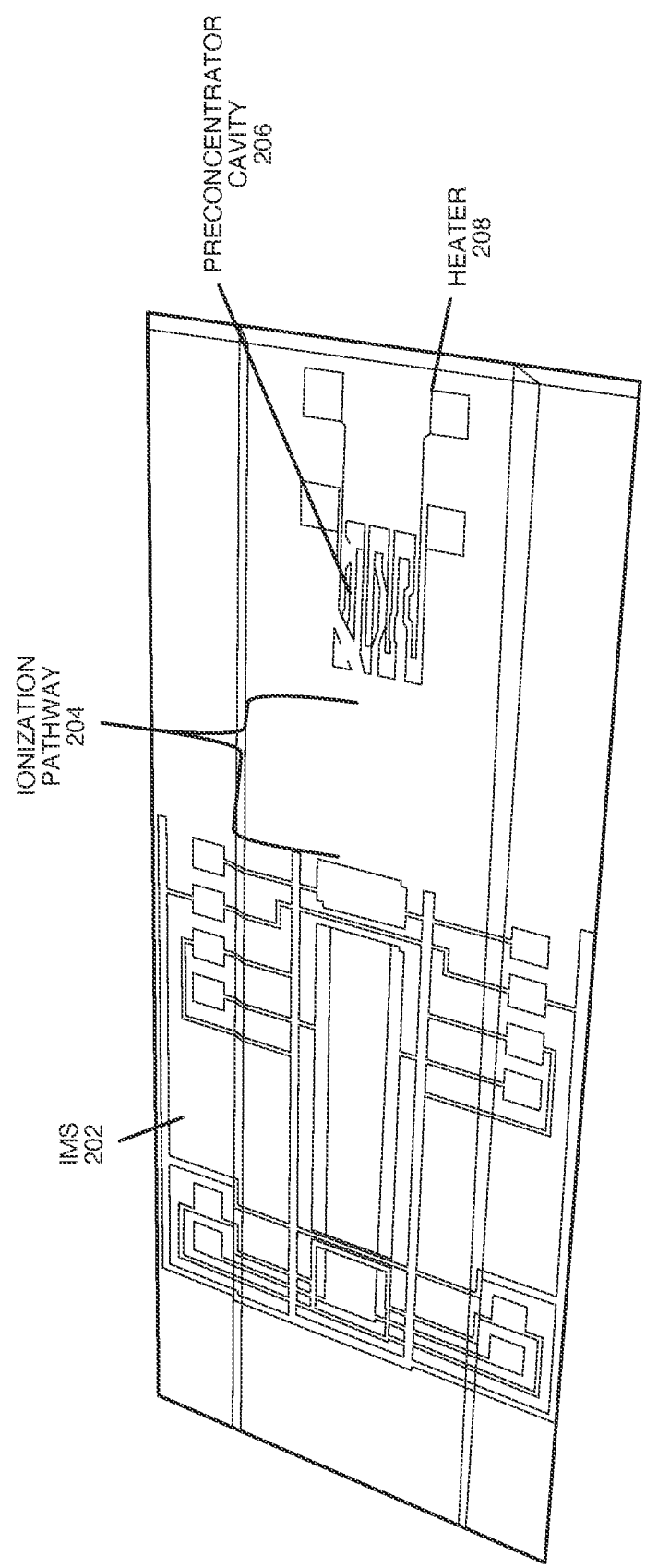
FIG. 2 presents a photograph of an exemplary chemical-analysis system in accordance with an embodiment of the present disclosure.

An exemplary implementation of chemical-analysis system 100 is illustrated in the photomicrograph that appears in FIG. 2. As illustrated in FIG. 2, the system includes a micro-preconcentrator comprising a preconcentrator cavity 206 and a heater 208. The output of this micro-preconcentrator feeds into an ionization pathway 204 and then into an ion-mobility spectrometer 202.

We now describe a number of application-specific variations of the chemical-analysis system 100 illustrated in FIGS. 1 and 2. In particular, we describe implementations associated with: (1) an unmanned aerial system (UAS), (2) a portable human-breath analyzer, and (3) a portable system for gathering agricultural samples.

Unmanned Aerial Vehicle Implementation

As mentioned above, a chemical-analysis system can be attached to an aerial platform (such as an unmanned aerial system (UAS), an airplane or a helicopter) and be used to sample, preconcentrate, separate, ionize, detect/measure and report on chemicals of interest as the aerial platform moves across space and time. This system can include any or all of the modules illustrated in FIG. 3, although the order and combination of these modules can be rearranged for a specific application. At the heart of this system is a chemical-detection module, which can comprise a HALF-IMS, but it might contain other detectors, including duplicate HALF-IMS modules, or IMS, DMS, FAIMS, IR, FTIR or other single-chemical detection modules.

Figure 3:
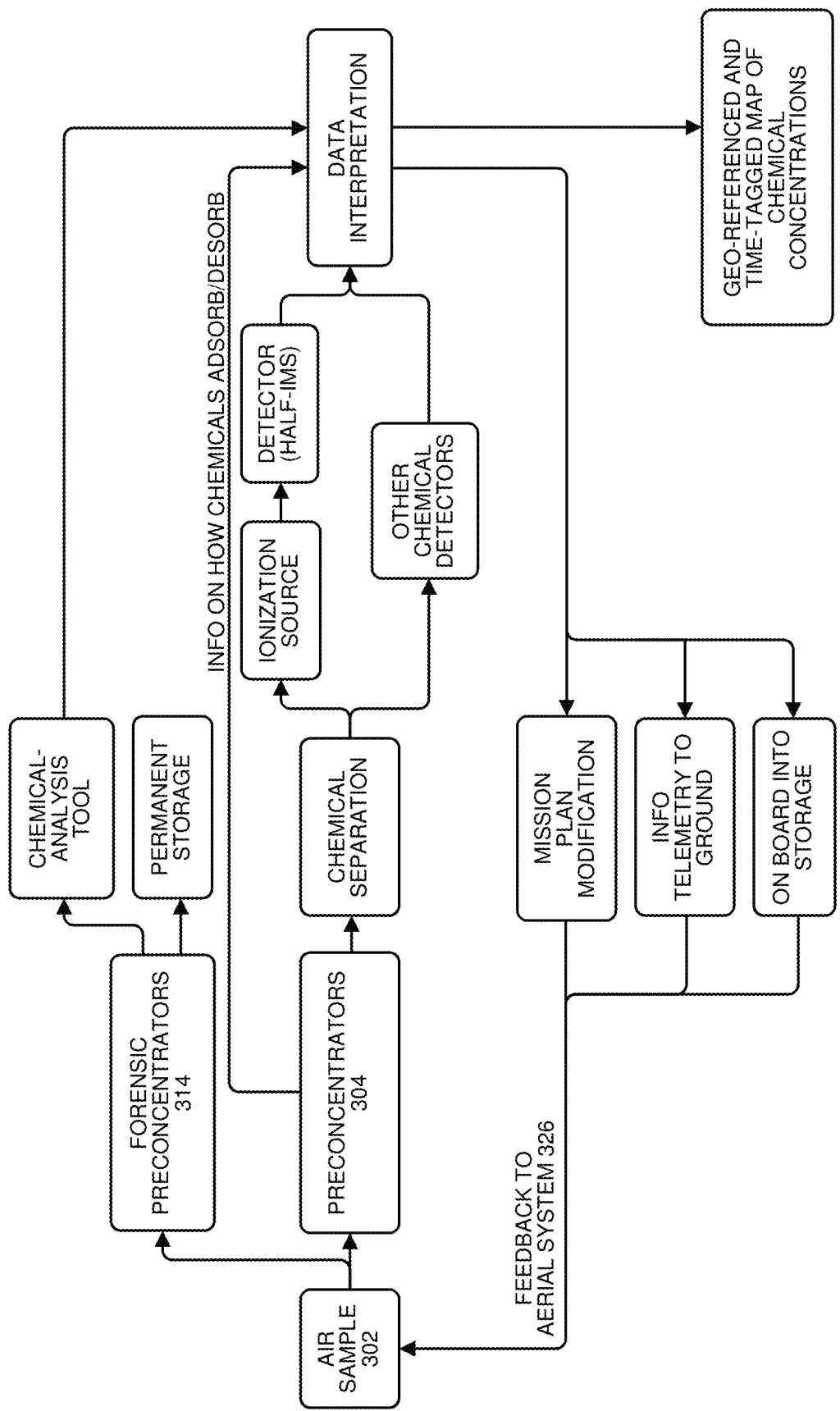
FIG. 3 presents a flow diagram for a chemical-analysis system in an unmanned aerial system (UAS) in accordance with the disclosed embodiments.

As illustrated in FIG. 3, an air sample 302 can be gathered by various passive or active mechanisms to bring an ambient air sample into the system for chemical analysis. These mechanisms can include: pumps, fans, and a system that creates static pressure differences, such as placement of an inlet in a flow field across an airfoil, etc. Preconcentrators 304 and 314 are used to preconcentrate gas-phase samples, which are encountered during the movement of the UAS. Preconcentrators 304 and 314 can include multiple micro-preconcentrators or miniature preconcentrators (µPC), which can be used to gather and store samples for future lab analysis, or alternatively can be coupled to one or more separators, ionization sources and detectors to provide real-time chemical analysis while in-flight. When stored on a preconcentrator, the air sample can be saved for forensic analysis at a later time. A pump can be used to move a sample into the adsorbing material of the preconcentrator. Factors such as sorbent type and device temperature during sampling can be controlled to promote capture of volatile compounds-of-interest over extraneous chemicals. Moreover, each preconcentrator can include an integrated heater to force release of the collected compounds to the ionization source/detector or lab system. The system can be powered via batteries or using the aerial system's power supply. Also, the preconcentrator can be produced using low-cost etching techniques involving glass substrates, or it can be fabricated onto metals, silicon or other substrates.

Multiple preconcentrators can be coupled and used in a single system, which allows each preconcentrator to sample separately or together as a group in parallel. This is particularly useful for UAS applications. The UAS can be programmed to sample at several geolocations separately with a different preconcentrator designated for each location and/or time point.

A control system provides instructions and feedback 326 for mission planning. For example, the UAS can be trained to follow increasing concentrations of chemicals. Moreover, the mission planning can be based on biologically inspired search techniques. Also, the chemical monitoring and/or sampling can be constant or intermittent.

The preconcentrator can be micro-fabricated along with a detector to make a multi-component system on a single chip. Moreover, the detector can feature one or more chemical detectors, such as an ion-mobility-spectrometry-based system containing an ionization source, a drift tube, and a current meter. An exemplary detector is a HALF-IMS.

The system can look for all chemicals present in a sample, or it can only look for chemicals that are of interest and are pre-programmed. It can also screen for types of chemicals (e.g. classes of chemicals), or uniquely identify them.

The sensing system components include a sampler, a preconcentrator, a microcontroller, at least one HALF-IMS, and a possible separation module. It can also include other types of chemical sensors. The system can additionally include other non-chemical sensors to detect: light, pressure, flow, humidity, etc. The system can also be designed to limit size and power requirements as allowed by the carrying aircraft.

The preconcentrator can be fabricated on low-cost glass substrates using traditional lithography along with wet-etching techniques to create a micro-channel for sample flow and a cavity to hold sorbent material. It can be alternatively manufactured on other substrates, and/or using other manufacturing techniques. The sorbent material can be carbon-powder-based, and can be chosen for a specific application of interest. A metalized pattern of electrodes on the back or front side of the preconcentrator comprises a resistive heater and temperature probes for each preconcentrator. A low-cost metal, such as tungsten, can be advantageously used to implement these electrodes due to its relatively close coefficient of thermal expansion to glass (4.3 versus 3.25 μm/m K), durability, and high temperature performance characteristics. To reduce the effects of oxidation, the tungsten film can be passivated using a thin layer of chromium. Note that other manufacturing methods can be used, as well as other materials.

The use of directly deposited heaters provides an efficient method to control the temperature of the sorbent bed. Depending on the application, heat can be applied rapidly to instantly desorb chemicals in the sorbent trap, or gradually to raise the temperature of the sorbent bed to control the release of different compounds at different time periods.

Figure 4A:
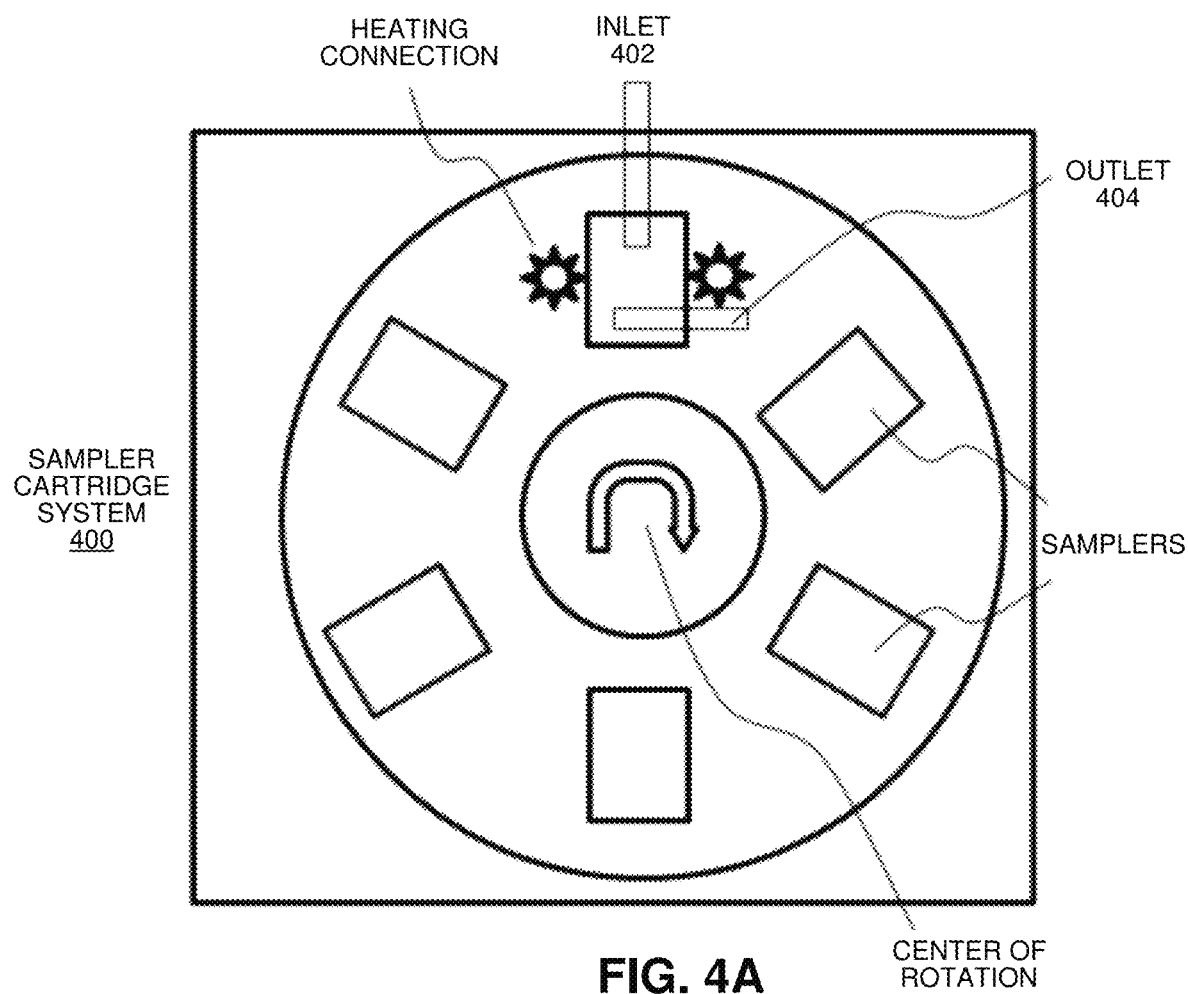
FIG. 4A illustrates a sampler cartridge system in accordance with the disclosed embodiments.

In the embodiment illustrated in FIG. 4A, a set of preconcentrators is implemented as a sampler cartridge system 400 comprising a movable "cartridge," which features the arrangement of one or more preconcentrators. Using a common pattern for air inlet/outlet locations on each preconcentrator, and perhaps embedded heaters, such as resistive heaters created by deposited metal, enables the use of a single pump. The system can also filter to eliminate certain particle sizes. Note that the system can move each sampler (comprising a preconcentrator) to interface with the inlet 402 and the outlet 404. This can be done with pre-knowledge of the ambient conditions, or in response to chemical information obtained from the system in-flight. Sampling time can be controlled via a microcontroller such that when sampling to a given preconcentrator is complete, it is moved away from the airflow interface and is hermetically sealed for future sample extraction and analysis. The next preconcentrator can then be used for sampling. The geolocation and time of each sample can be recorded to facilitate creating a map across an area, which can be used to track a toxic plume or other chemical emissions.

Figure 4B:
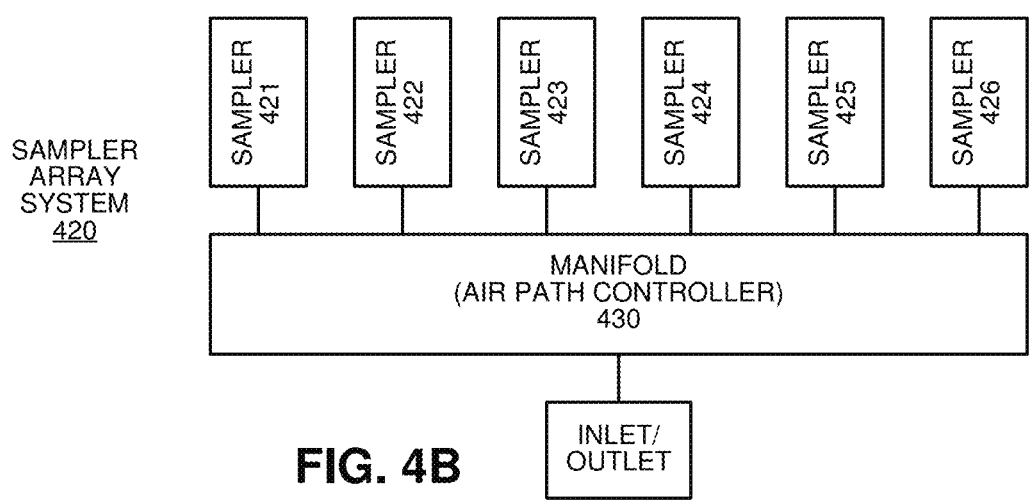
FIG. 4B illustrates a sampler array system in accordance with the disclosed embodiments.

In a second embodiment illustrated in FIG. 4B, a sampler array system 420 comprises an array of samplers (containing preconcentrators) 421-426, which are linked in parallel using tubing and solenoids and/or a manifold 430 to vary flow into the devices across space and time. Unlike the previous embodiment, this embodiment does not include moving components. Instead, a microcontroller (not shown) is used to specify which preconcentrator receives the sample airflow for a given time period.

In both of the preconcentrator implementations described above, it is possible to create a system that facilitates sampling to multiple preconcentrators concurrently, or sequentially. This provides a way to gather sample replicates when an application requires them. After the sample is collected, it can be returned to a base location where chemicals retained on preconcentrators can be analyzed using traditional bench top chemical-analysis techniques. The system can alternatively be interfaced with a chemical-detection system, such as an ion mobility spectrometer or a HALF-IMS, to perform real-time chemical analysis while the UAS is in-flight. A microcontroller can power and direct the heaters and the analysis can be performed after the sample is collected without requiring user input, perhaps while the UAS is flying to its next sampling location. Decisions on mission planning can be made autonomously based on chemical information obtained in-flight.

Coupling the chemical detection system to a UAS provides additional advantages. The system can be powered using the UAS's power supply and controlled using the UAS's control system. This facilitates sampling at multiple locations during a single flight, wherein a separate preconcentrator can be used for each location. The preconcentrators can be the same, or can have variations that are tailored for each sampling location or for increased sampling breadth. The flight path can be automated by using GPS coordinates and timestamps for sampling locations and prescribing the time for sampling at each sampling location. After the sampling is complete, the UAS can return to a base location and the preconcentrators can be taken to a lab for subsequent analysis. Various applications can make use of such sampling capabilities, including: surveying of farm land or other biological ecosystems, detection of harmful or controlled substances, and air quality monitoring. Moreover, samples collected for later forensic use can be uniquely numbered (e.g., barcoded) so that they can be tracked and the information can be assembled into a bigger picture of the surveyed region The preconcentrator can be fabricated as a single chip with a detector, such as a HALF-IMS or an ion mobility spectrometer. In such an embodiment, the chip contains a sorbent bed and a channel for preconcentration. Teflon film can be used to bond substrate halves together to form channels and/or interconnects between different devices. This process can be carried out by heating the film to ~280°

C. and applying approximately 5 PSI of pressure for five minutes. The result is a chip, which is amenable to multi-layer structuring. The outflow from the preconcentration step can be ionized by an ionization source, and can be fed through a drift tube to a detector. The small device feature size allows for a reduction of dead volume, thereby improving the efficiency of analysis and reducing ion loss. Integrated heaters can also be used to ensure that the temperature is uniform throughout the device channels, which allows analytes to remain in the gas phase and not condense on the channel walls due to local cool areas.

Specific features of the system include the following.

Materials/Fabrication: The preconcentrator can be made of glass and can be filled with off-the-shelf sorbents. Metalized layers (including tungsten) can help achieve temperature control.

Concentration Factor: A concentration in the range from parts-per-trillion (ppt) to parts-per-billion (ppb) (a 1000× concentration) can be achieved with a sampling time of 2 min. However, if the sampling time is increased substantially (e.g., >5 min), then a 10,000× concentration is possible. Note that the amount of VOCs captured can be increased by substantially increasing this sampling time.

Selectivity and Specificity: Selectivity to certain analytes can be altered by changing the sorbent material used. A carbon-based multi-purpose sorbent is suitable for a wide range of VOCs. However, true specificity to a single analyte is difficult to achieve with most sorbent materials used in preconcentration devices; chemical separation and identification is typically performed by the detection system.

Form Factor: The system can use a carrier gas in an outgas step to ensure that the sample goes from the preconcentrator to the detector. The preconcentrator and detector can also be integrated into a single chip.

Power Usage: The system can be powered using a stand-alone battery or can be coupled to the power supply of the UAS.

Portable Breath Analyzer Implementation

We now describe an implementation of a device called a "humidity micro-preconcentrator (HuPC)," which is designed for human-breath sampling and is associated with a workflow for collecting volatile organic compounds (VOCs) from complex mixtures in a high-humidity ambient such as exhaled breath. An exemplary HuPC is illustrated in FIG. 5A. The HuPC includes a number of novel design features, including: (1) an electrode arrangement that faces the adsorbent cavity to decrease power consumption; (2) water rejection within a specifically designed molecular sieve cavity; (3) inclusion of temperature and humidity sensors to trigger environmental or breath sampling conditions; (4) potential use of a fractal structure for metal electrodes; and (5) use of micro-pillar structures to define the cavities and as stoppers for the adsorbents. Moreover, this HuPC device is designed to be portable, easy to use and inexpensive to manufacture.

The HuPC device is designed to collect VOCs from exhaled breath. A pump can be added at the rear of the HuPC to provide external pressure, which is likely to be required during breathing from a resting state. The HuPC device can also include an inert polytetrafluoroethylene mouthpiece and tube connected to the micro-preconcentrator (HuPC), which can be made of silicon and inert glass using microfabrication techniques. However, other sampling materials and configurations can be used.

The portable HuPC device is designed to collect VOCs having different chemical structures and polarities by using consecutive cavities, which are separated by micro-pillars. As illustrated in FIG. 5B, deep micro-channels (and associated micro-pillars) can be micro-machined in the substrates using low-cost wet etchants or other microfabrication or manufacturing techniques. These micro-pillars can be used as cavity definers and adsorbent stoppers. The glass can be used as enclosure and support for the micro heaters, and also for the humidity and temperature sensors. However, other substrate materials can also be used. Moreover, different materials can be used for the electrodes, including platinum, gold or tungsten. Humidity and temperature sensors located at the inlet are included to indicate when a breath sample is being collected. The proposed sensing medium of the humidity sensor of the HuPC is polyimide, but other sensing media can be used.

It is possible to use off-the-shelf adsorbents, with a single adsorbent per cavity, or with multiple combinations of adsorbents, which can be used to adsorb/absorb specific compounds-of-interest. Additionally, multiple-stack HuPCs with single or multiple adsorbents are feasible. Also, one of the cavities can be used with a molecular sieve to retain the water content of the sample. During system operation, the collection temperature can be maintained within a narrow range to ensure sample-to-sample reproducibility between breaths and between people. The collected VOCs can be subsequently desorbed and analyzed using appropriate analytical chemistry techniques for the analyte composition.

Adsorbed compounds can be released from the HuPC by a thermal pulse or by ramping the temperature to have gas-chromatograph-like profiles provided by a novel metal electrode design. In some embodiments, the electrodes (and also the humidity and temperature sensors) are facing the adsorbents, so less power is required to heat them. This removes unnecessary thermal mass in comparison to traditional electrode arrangements on the opposite side of the silicon or glass or other substrate.

With regard to materials and fabrication, the preconcentrator can be made of silicon and glass (or other substrate) and can be filled with off-the-shelf commercial sorbents. Custom sorbents for specific chemicals can also be used. Several cavities define the HuPC, wherein each cavity contains micro-pillars at the inlet and outlet that support and contain the adsorbents. Electrodes comprising metalized layers can be comprised of various materials, such as platinum, gold and tungsten (or other metal) to help to achieve temperature control. Note that the electrodes face the cavities, which decreases the power required to desorb the retained VOCs. Optical energy can also be used for temperature control. The capacitive humidity sensing material can be polyimide, but different materials can be used.

Selectivity to certain analytes can be altered by changing the sorbent material used. For example, different powder-based inorganic or carbon-based multi-purpose sorbents can be used to enable preconcentration of a wide range of VOCs of different sizes and chemical structures. Also, different adsorbents can be used to promote retention of specific VOCs, and molecular sieve sorbents can be used to reduce water content.

This device can be connected in series with various components, including: chemical ionization sources, samplers, and chemical detectors to facilitate near-real-time analysis. This device can also be used for forensic concentration and sampling of breaths for later analysis at a different location. The geolocation and time can be annotated to correspond with the breath sample.

This device can be also connected with a smart device or personal mobile device, such as a cell phone for breath sampling and monitoring. This device can also be tailored for other high-humidity ambient or contained environments, or for nonhuman (e.g., animal) breaths.

Figure 5C:
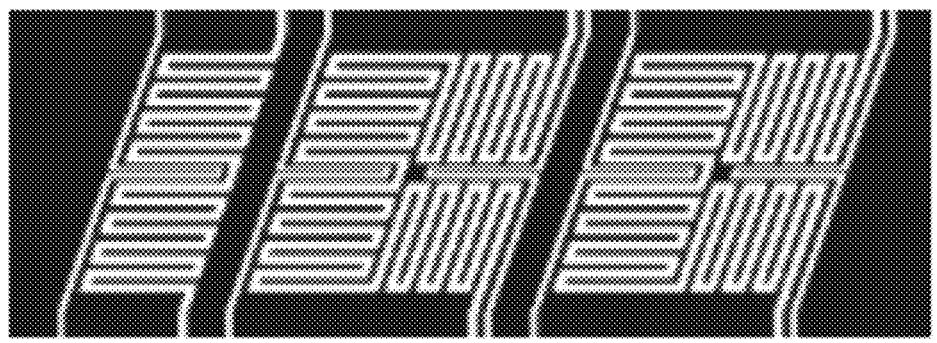
FIG. 5C presents a diagram of a resistive heater and temperature sensor pattern for a preconcentrator in accordance with the disclosed embodiments.

Advantages of the proposed breath micro-preconcentrator include: (1) the possibility of miniaturization; it is expected that the device can be packaged within a cell phone form factor; (2) the decreased power consumption resulting from design solutions of arranging the electrodes to face the adsorbent cavity; (3) the capability of operating in a high-humidity environment achieved by the water content rejection within a specific molecular sieve cavity; (4) inclusion of temperature and humidity sensors to trigger ambient or breath sampling conditions; (5) usage of metal electrodes with a fractal structure (as illustrated in FIG. 5C) to increase the heating factor compared to plain or other electrode configurations; and (6) the use of micro-pillar structures to define the cavities and serve as stoppers for the adsorbents. Finally, the device is designed to be portable, easy to use and inexpensive to manufacture.

Agricultural Implementation

An alternative implementation is useful for agricultural applications, such as: detection of VOCs that are outgassed from plants in a greenhouse or an orchard setting; post-harvest monitoring and monitoring agricultural products during transport/storage/shipment; and assessing the quality of an agricultural product, in terms of flavor or aroma.

This agricultural implementation can include one or more micro-preconcentrators (µPC), which can each be used to gather and store a sample for future lab analysis. It can also be coupled to one or more mobile ionization sources and mobile, detectors for real-time analysis at a point-of-testing. A pump can be used to move a sample into the adsorbing material of the µPC. Factors such as sorbent type and the device temperature during sampling can be controlled to promote capture of volatile organic compounds (VOCs) of interest over extraneous chemicals. Each preconcentrator can feature an integrated heater to force release of the collected compounds to the ionization source/detector or lab system, with a design that uniformly heats the active area. Each preconcentrator can also feature an integrated temperature sensor for feedback-based temperature control, allowing for temperature and time-based chemical separation, similar to a miniature or full-sized gas chromatograph. An external cooling supply can also be used to allow for faster sampling ability. The system can be powered via batteries, or an alternative portable method. The preconcentrator can be fabricated using microfabrication etching techniques on a silicon substrate, or by finely controlled additive manufacturing techniques. Each preconcentrator can feature porous micro-structures for increased surface area, and can use microfabrication plating methods to coat an adsorbent material that is tailored to the specific analytes of interest.

In general, the preconcentrator can be fabricated using various substrates, with traditional processing methods such as photolithography along with etching to create a micro-channel for sample flow and a cavity with high-aspect-ratio porous microstructures to hold sorbent material. Metalization can be used to pattern electrodes, which comprise heating elements and temperature probes for each preconcentrator. The use of directly deposited heaters provides an efficient method of temperature control of the sorbent bed, but externally bonded components can be alternatively used. Depending on the application, heat can be applied rapidly to instantly desorb chemicals in the sorbent trap, or can be applied gradually to raise the temperature of the sorbent bed to control the release of different compounds during different time periods. A low-cost metal such as tungsten can be used due to its relatively close coefficient of thermal expansion to silicon (4/0.3 versus 2.6 µm/m K), durability, and high temperature performance characteristics. To reduce the effects of oxidation, the tungsten film can be passivated using a thin layer of chromium. Alternatively, gold may be used during a plating step.

With regard to materials and fabrication, multiple preconcentrators can be fabricated on a single substrate, and the channel for sample flow can be created by etching. Patterned metalized layers (e.g., tungsten or gold) can be used to form a resistive heater network and a temperature-coefficient-of-resistance-based temperature sensor, allowing for temperature control. Also, an external cooling supply can be used to rapidly cool the device after thermal desorption, and a humidity sensor and a desiccant material may also be used to control moisture in the sample.

A concentration factor of greater than 1000× can be achieved for a short sampling time on the order of 2 min. However, the amount of VOCs captured can be further increased by substantially increasing the sampling time.

Moreover, selectivity to certain analytes can be altered by changing the adsorbent material. The adsorbent material is expected to be derived from a thiol compound, but may also be Tenax TA, or a carbon-based adsorbent. However, true specificity to a single analyte is difficult to achieve with most sorbent materials used in preconcentration devices. Note that chemical separation and identification is typically performed by the detection system. High levels of temperature control can potentially be used for time-based separation of chemicals without an additional gas chromatography system.

Also, a carrier gas can be used during an "outgas step" to ensure that the sample goes from the preconcentrator to the detector.

Process of Operating a Preconcentrator

Figure 6:
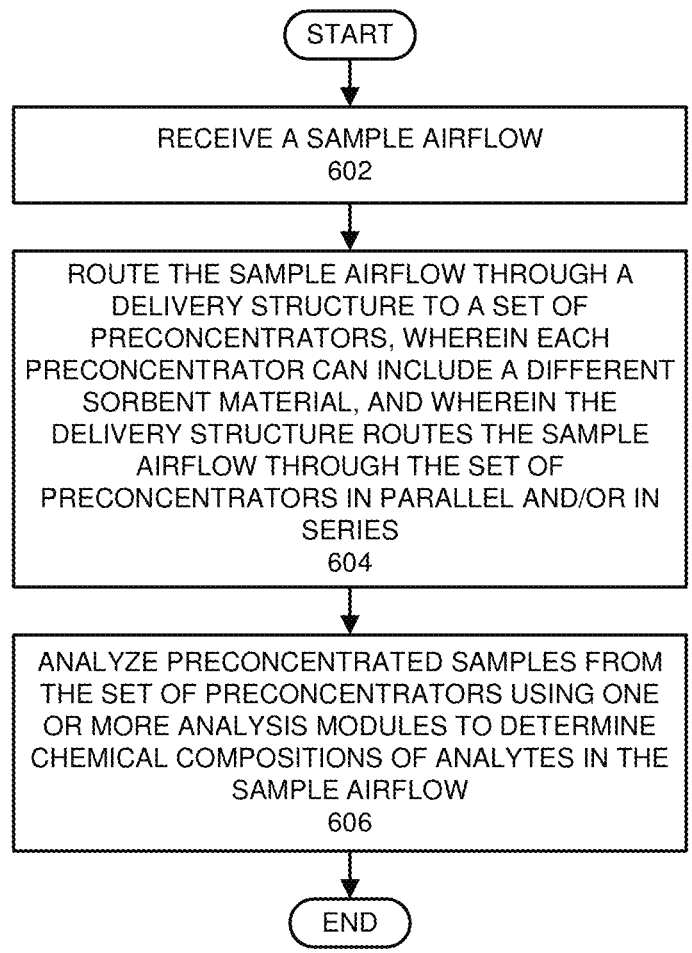
FIG. 6 presents a flow chart illustrating operations performed by a preconcentrator in accordance with the disclosed embodiments.

FIG. 6 presents a flow chart illustrating operations performed by a preconcentrator in accordance with the disclosed embodiments. First, the system receives a sample airflow (step 602). Next, the system routes the sample airflow through a delivery structure to a set of preconcentrators, wherein each preconcentrator can include a different sorbent material, and wherein the delivery structure routes the sample airflow through the set of preconcentrators in parallel and/or in series (step 604). Finally, the system analyzes the preconcentrated samples from the set of preconcentrators using one or more analysis modules to determine chemical compositions of analytes in the sample airflow (step 606).

Shipping Container

Figure 7:
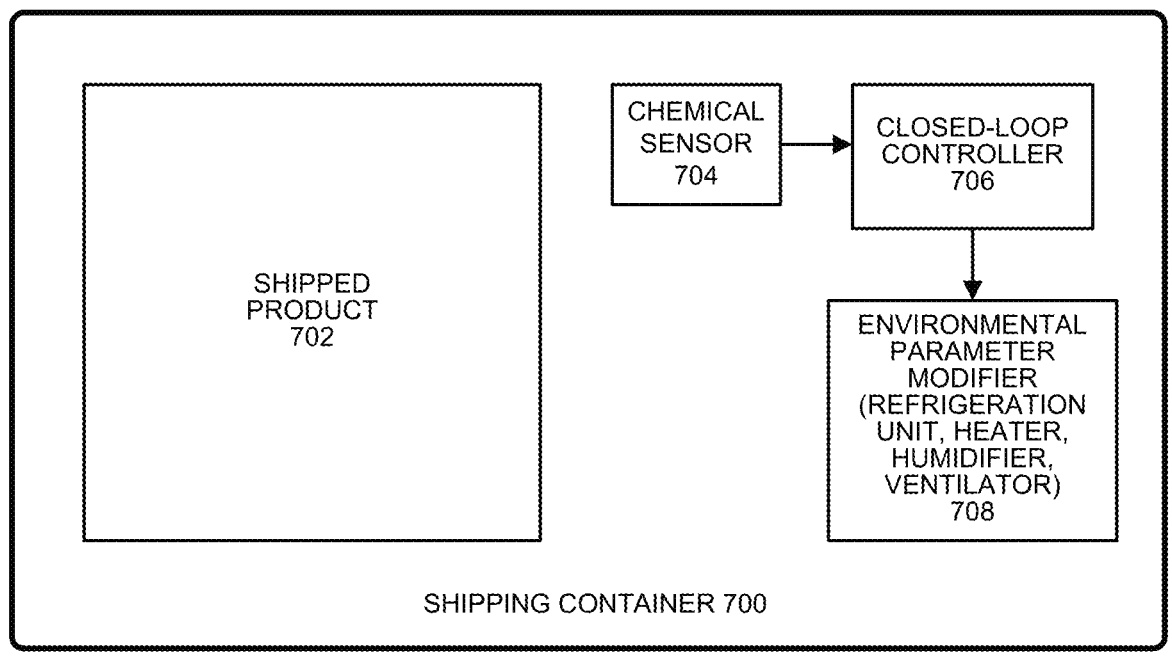
FIG. 7 illustrates a shipping container with a closed-loop environmental control system in accordance with the disclosed embodiments.

The above-described portable chemical-analysis system can be used in a variety of applications including in a closed-loop control system to control environmental parameters within a shipping container, such as a refrigerated shipping container, which is used to transport perishable products. For example, FIG. 7 illustrates a shipping container 700 with a chemical-based closed-loop environmental control system in accordance with the disclosed embodiments. As illustrated in FIG. 7, shipping container 700 contains a shipped product 702, which is sensitive to environmental parameters, such as temperature and humidity. It also includes a chemical sensor 704, which detects and analyzes off-gassed chemicals from shipped product 702. Readings from chemical sensor 704 feed into a closed-loop controller 706, which uses the readings to perform closed-loop control of an environmental parameters modifier 708, such as a refrigeration unit, a heater, a humidifier, or a ventilator.

Closed-loop controller 706 is used to implement a closed-loop control system, which uses chemical sensor 704 to monitor volatile compounds, especially volatile organic compounds (VOCs) emitted by shipped product 702. This enables closed-loop controller 706 to effectively control material storage conditions within shipping container 700. Closed-loop controller 706 uses closed-loop control techniques to control environmental variables, such as temperature, humidity, and air circulation, while the shipped product 702 changes its VOC profile over time and in response to the environmental variables. During operation, chemical sensor 704 continuously monitors the VOC profile and when it changes, closed-loop controller 706 changes how the environment is maintained to achieve certain outcomes such as preventing spoilage of perishables.

In one example, when bananas or other produce are shipped they are kept in temperature-controlled and often environmentally controlled containers to prevent premature ripening. At the point of harvest, unripe bananas are packed into a refrigerated shipping container and held at a low temperature to prevent ripening. This uses a lot of energy, which might not really be needed because the temperature control is not based on any physical information from the banana other than the minimum temperature that bananas can tolerate without suffering permanent damage, and the date the banana was harvested. In contrast, in a refrigerated container that uses a VOC-sensor-based environmental control system, the initial setpoint temperature could be set higher than the minimum that the bananas can tolerate, and the system could have a relatively large acceptable range of temperatures. Note that the VOC sensor system can be placed next to the refrigeration unit outside of the temperature-controlled portion of the container. The sensor could then sample from the air before it passes through the refrigeration unit. If the VOC sensor system detects compounds that indicate the bananas are ripening, it can send a signal to the temperature controller to either lower the setpoint temperature (which can either be incrementally lowered or immediately lowered to the minimum acceptable setpoint), or adjust the control technique to minimize temperature variations. The setpoints can be adjusted to achieve the desired level of ripening at the final shipping destination.

This type of shipping container facilitates enhanced supply chain management, and potentially reduced storage times prior to the commodity arriving at the point-of sale. Based on VOC data, the temperature (or air flow) setpoints during the shipping process may be adjusted to minimize energy usage. The VOC information can also be used to shut off refrigeration during shipment if the VOC information indicates that the product has spoiled, and can be abandoned to save energy. The VOC data can also be provided to end users to validate shipment quality control at all times and locations in the supply chain for a product. The VOCs can also be associated with steps on a pack line for postharvest sorting and shipping (e.g., sorting for various stages of ripeness).

In another example, the system reduces energy consumption in refrigerated shipping containers by using closed-loop control systems along with chemical sensors. In this example, we will monitor for VOC signatures off-gassed from food products in a shipping container as indirect indicators of quality and freshness. This information is used to provide feedback to decrease/increase cooling capacity and/or ventilation within the shipping container over time.

By implementing this sensor feedback into a closed-loop control system, the system is better able to tailor the cooling profile of the container to both optimize energy consumption as well as stably maintain the cargo at its optimum temperature over the duration of a shipment. As the food or produce in the container changes over time (as detected by their VOC profiles), the container environment can be optimized in near-real-time, without using energy for unnecessary cooling when it is not needed.

Note that VOCs are very good indicators of post-harvest food quality, and specific off-gassed compounds have been identified in many food stuffs that are linked to age, ripeness, and quality of storage conditions. Current shipping container conditions are almost always held at temperatures much lower than needed to ensure proper food storage. This extra "insurance" cooling allows the shipping industry to guarantee shipment conditions to growers at the point-of-harvest. However, the extra power consumption due to this cooling "insurance" can be dramatically reduced if the temperature setpoint of the container can be dynamically adapted in response to cargo quality, instead of artificially setting static low temperatures for the duration of the voyage.

By detecting a multitude of off-gassed chemical compounds from food at the same time, the system enables a more reliable assessment of produce cargo freshness and the corresponding need of storage condition adjustments in near-real-time. The abundance of these measured VOCs can be used to tune a "smart" refrigerated cargo shipping system to reduce energy consumption and simultaneously maintain the cargo by dynamically adjusting the container ambient conditions.

The shipping container can also be controlled to reduce food spoilage. In addition to single compounds (like ethylene) that indicate food spoilage, the actual spoilage bacteria itself frequently contributes to the ultimate mixture of volatiles generated by produce cargo. Detection of microorganism-specific volatiles can serve as one of the most important indications of additional cooling demand for improved storage conditions. For example, *Pantoea agglomerans* and *Rahnella aquatilis* are both species of spoilage bacteria that have been isolated from mixed lettuce. Each bacteria strain produces a range of VOCs such as: ethanol, ethyl acetate, 2-methyl-1-propanol, 2-methyl-1-butanol, 3-methyl-1-butanol, 2,3-butanedione, 3-methyl-1-pentanol, 1-butanol and 1-hexanol. Under optimized storage conditions (e.g., airtight packing at 7° C.), 2-methyl-1-butanol, 3 methyl-1-butanol and ethanol are produced alone by the spoilage microorganisms. If high concentrations of the above-listed compounds are reached on the cut surfaces of shredded mixed lettuce, the quality of the shredded mixed lettuce can be negatively influenced by the microbiological production of metabolites. Hence, detection of these compounds at an early stage can serve as a signal for the modification of storage conditions, thereby saving the shipment and allowing for human consumption.

Likewise, a complex mixture of "alarm" volatiles are also known to be produced during fish and meat spoilage. For example, in fish such as whiting (*Merlangius merlangus*), cod (*Gadus morhua*) and mackerel (*Scomber scombrus*), as many as 86 VOCs have been previously simultaneously identified. A total of 20 of these could be used to characterize "freshness" including: alcohols, ketones, aldehydes and C2-C11 esters. Detection of meat spoilage is also possible by measuring VOCs. The concentrations of multiple VOCs, particularly sulfur compounds, tend to increase over the storage time. Some compounds, such as ethanol, are more generally produced in various perishables during storage, and are present in greater amounts under non-optimal storage conditions. In fact, empirical evidence shows that a VOC-based metabolic profiling approach possesses enough discriminatory information to differentiate naturally spoiled pork from pork contaminated with *Salmonella typhimurium*, a food poisoning pathogen commonly recovered from pork products.

Chemical analysis of mixtures of volatiles can provide comprehensive information regarding cargo freshness and the need for storage condition adjustment. However, the data may be excessively complex to directly interpret. To remedy this problem, data-mining and advanced signal-processing techniques can be used for pattern recognition associated with spoilage prediction.

Figure 8:
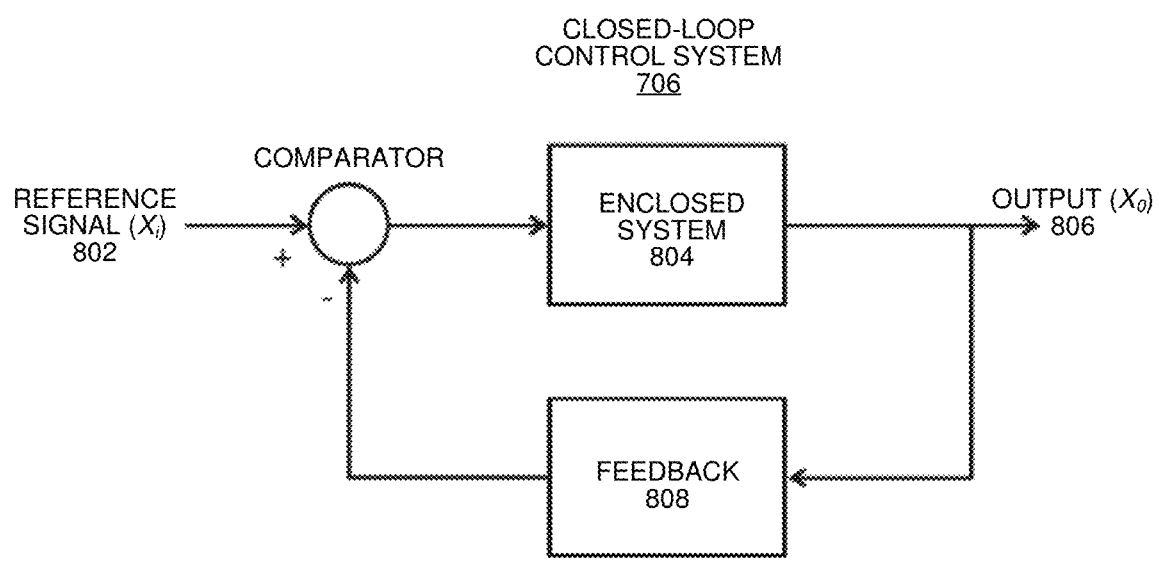
FIG. 8 illustrates a closed-loop environmental control system in accordance with the disclosed embodiments.

We now describe closed-loop control system 706, which is illustrated in more detail in FIG. 8. As illustrated in FIG. 8, a chemical sensor in enclosed system 804 generates an output $X_0$ 806, which provides feedback 808, which is compared against a reference signal $X_i$ 802. When the chemical sensor system detects a specific compound or composite changes in the volatiles profile, an adjustment is made either to the reference signal $X_i$ or to the feedback loop.

For the system to operate, at least one environmental variable must be closed-loop controlled (e.g., temperature, humidity, light, etc.) through a microcontroller or some other adjustable control method. The control system can either be continuous (PID, H2, etc.) or discrete (on-off control, etc.). Inside enclosed system 804, there is a product whose off-gassed volatile profile varies over time and due to the environmental variables. An example is perishable material such as food in a refrigerator that may emit volatiles due to onset of spoilage, ripening (e.g., for produce), etc. In this case, closed-loop control system 706 aims to maintain adequate storage conditions while avoiding excessive cooling, which requires a large energy expenditure. The system tries to maintain a reference profile signal $X_i$ 802 to prevent spoilage-specific compounds from arising. Depending on the complexity of the profile signal, a computer (e.g., in smartphone form or a portable factor) may need to be used to process the data and compare it against the reference signal. When the sampled signal varies from the reference signal, the computer sends a signal to an environmental controller to adjust the control parameters.

Operating a Control System in a Shipping Container

Figure 9:
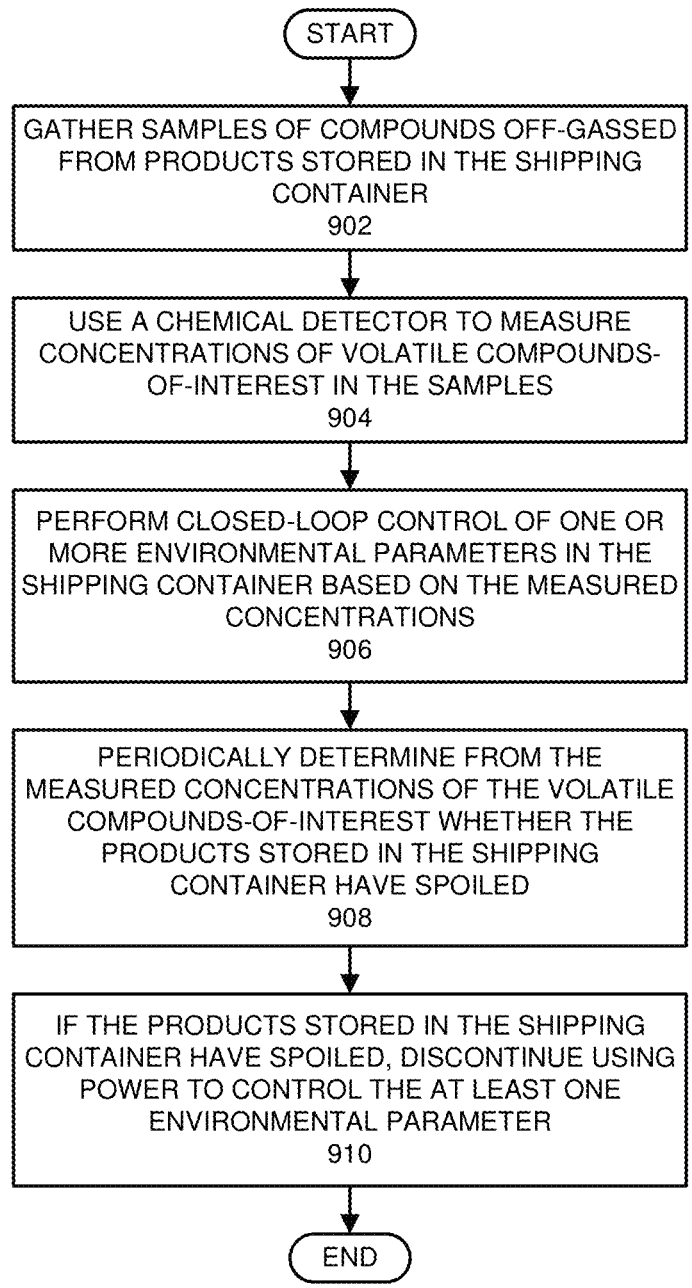
FIG. 9 presents a flow chart illustrating operations performed by a closed-loop environmental control system within a shipping container in accordance with the disclosed embodiments.

FIG. 9 presents a flow chart illustrating operations performed by a closed-loop environmental control system within a shipping container in accordance with the disclosed embodiments. First, the system gathers samples of compounds off-gassed from products stored in the shipping container (step 902). Next, the system uses a chemical detector to measure concentrations of volatile compounds-of-interest in the samples (step 904). The system then performs closed-loop control of one or more environmental parameters in the shipping container based on the measured concentrations (step 906). During operation, the system periodically determines from the measured concentrations of the volatile compounds-of-interest whether the products stored in the shipping container have spoiled (step 908). If the products stored in the shipping container have spoiled, the system discontinues using power to control the at least one environmental parameter (step 910).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A portable breath analyzer system, comprising:
    a preconcentrator comprising:
        a substrate that is micro-machined to include consecutive cavities containing sorbent materials;
        wherein, during a sampling operation, a gas phase sample passes through the consecutive cavities containing the sorbent materials; and
        wherein the consecutive cavities are separated by microstructures that do not impede a gas flow of the gas phase sample, while ensuring that the gas flow does not cause the sorbent materials to escape from the consecutive cavities;
    a mouthpiece and a tube coupled to the preconcentrator for receiving human breath samples; and
    a chemical detector operably connected to the preconcentrator.

2. The system of claim 1, wherein each of the consecutive cavities in the preconcentrator includes an inlet and an outlet, and wherein the microstructures at the inlet and the outlet function to support and contain the sorbent materials in the cavity.

3. The system of claim 1, wherein each of the consecutive cavities in the preconcentrator holds a different type of sorbent material.

4. The system of claim 1, wherein one or more of the consecutive cavities in the preconcentrator is in communication with a molecular sieve to retain water content from a sample.

5. The system of claim 1, further comprising a humidity sensor and/or a temperature sensor located at an inlet of the preconcentrator.

6. The system of claim 1, further comprising an integrated heater in the preconcentrator that triggers a release of absorbed compounds from the sorbent material.

7. The system of claim 6, wherein the integrated heater is controlled using a feedback-based temperature control technique.

8. The system of claim 1, wherein—the microstructures comprise micro-pillars.

9. The system of claim 6, wherein the integrated heater includes electrodes having a fractal structure.

10. The system of claim 1, further comprising a pump to facilitate moving a sample through the preconcentrator.

11. The system of claim 1, wherein the chemical detector includes a gas chromatography (GC) system.

12. The system of claim 1, wherein the chemical detector includes a differential mobility spectrometer (DMS).

13. The system of claim 1, wherein the chemical detector includes a high asymmetric longitudinal field ion mobility spectrometer (HALF-IMS).

14. The system of claim 1, wherein the chemical detector includes a high field asymmetric ion mobility spectrometer (FAIMS).

15. The system of claim 1, further comprising an ionization source operably connected to the preconcentrator.

* * * * *